(12) United States Patent
Liu et al.

(10) Patent No.: US 7,343,804 B2
(45) Date of Patent: Mar. 18, 2008

(54) WIRELESS ACOUSTIC WAVE SENSOR SYSTEM FOR USE IN VEHICLE APPLICATIONS

(75) Inventors: James Z T Liu, Hudson, NH (US); Steven J. Magee, Lena, IL (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/274,786

(22) Filed: Nov. 14, 2005

(65) Prior Publication Data

US 2007/0107519 A1 May 17, 2007

(51) Int. Cl.
*G01N 29/00* (2006.01)
*G01M 17/00* (2006.01)

(52) U.S. Cl. ............... 73/649; 73/146; 701/29

(58) Field of Classification Search ............ 73/649, 73/703, 715, 146, 579, 602; 72/702; 702/77, 702/140, 188; 701/38, 29
See application file for complete search history.

(56) References Cited

U.S. PATENT DOCUMENTS

| | | | | |
|---|---|---|---|---|
| 4,384,409 A | * | 5/1983 | Lao ............... | 33/318 |
| 4,467,235 A | * | 8/1984 | De Wames et al. ..... | 310/313 D |
| 4,512,198 A | | 4/1985 | Sinha et al. ............ | 73/703 |
| 4,586,382 A | | 5/1986 | Sinha ................. | 73/703 |
| 4,622,854 A | | 11/1986 | Locke et al. ............. | 73/703 |
| 4,622,855 A | | 11/1986 | Sinha et al. .............. | 73/703 |
| 4,746,830 A | * | 5/1988 | Holland ................ | 310/313 D |
| 5,117,146 A | * | 5/1992 | Martin et al. ............ | 310/313 R |
| 5,359,250 A | * | 10/1994 | Toda .................... | 310/313 R |
| 5,488,866 A | | 2/1996 | Ravel et al. ............ | 73/579 |

(Continued)

FOREIGN PATENT DOCUMENTS

EP 0518900 B1 12/1992

(Continued)

OTHER PUBLICATIONS

L. Reindl, G. Scholl, T. Ostertag, H. Scherr, U. Wolff, F. Schmidt, *Theory and Application of Passive SAW Radio Transponders as Sensors*, IEEE Transactions on Ultrasonics, vol. 45, No. 5, Sep. 1998.

(Continued)

*Primary Examiner*—Helen Kwok
(74) *Attorney, Agent, or Firm*—Kermit D. Lopez; Luis M. Ortiz; William B. Shelby (57) ABSTRACT

An acoustic wave sensor system, comprising a plurality of acoustic wave sensing devices for detecting a multiplicity of varying conditions wherein each acoustic wave sensina device among the plurality of acoustc wave sensing devices is an independent component for detecting at least one condition of the multiplicty of varying conditions and a common interrogation component that communicates with each acoustic wave sensing device among the plurality of acoustic wave sensor devices for providing an interrogation signal to each acoustic wave sensing device thereof. A transmitter and receiver unit can also be provided that communicates with the common interrogation component and the plurality of acoustic wave sensing devices and which transmits an interrogation signal from the common interrogation component to the at least one acoustic wave sensing device among the plurality of acoustic wave sensing devices and which receives sensor data from at least one acoustic wave sensing device.

20 Claims, 5 Drawing Sheets

U.S. PATENT DOCUMENTS

| | | | |
|---|---|---|---|
| 5,821,425 A | 10/1998 | Mariani et al. | 73/703 |
| 6,144,332 A * | 11/2000 | Reindl et al. | 342/42 |
| 6,424,238 B1 | 7/2002 | Penunuri | 333/187 |
| 6,609,430 B1 | 8/2003 | Joshi et al. | 73/861.25 |
| 6,621,192 B2 * | 9/2003 | Lu et al. | 310/313 A |
| 6,664,708 B2 * | 12/2003 | Shlimak et al. | 310/313 R |
| 6,738,697 B2 | 5/2004 | Breed | 701/29 |
| 6,848,295 B2 | 2/2005 | Auner et al. | 73/24.06 |
| 6,914,279 B2 | 7/2005 | Lu et al. | 257/252 |
| 6,958,565 B1 * | 10/2005 | Liu | 310/313 R |
| 6,965,217 B2 * | 11/2005 | Dohnal et al. | 323/257 |
| 7,017,416 B1 * | 3/2006 | Liu et al. | 73/702 |
| 7,065,409 B2 * | 6/2006 | Mazar | 607/60 |
| 7,065,459 B2 * | 6/2006 | Kalinin et al. | 702/77 |
| 2002/0015452 A1 | 2/2002 | Chai et al. | 375/316 |
| 2002/0021193 A1 | 2/2002 | Chai et al. | 333/187 |
| 2002/0027397 A1 | 3/2002 | Chai et al. | 310/313 R |
| 2003/0009270 A1 | 1/2003 | Breed | |
| 2004/0135675 A1 | 7/2004 | Thiesen et al. | |
| 2004/0239504 A1 | 12/2004 | Kalinin et al. | |

FOREIGN PATENT DOCUMENTS

| | | |
|---|---|---|
| EP | 0937615 A2 | 8/1999 |
| JP | 59060332 A | 4/1984 |
| WO | WO 91/13832 | 9/1991 |

OTHER PUBLICATIONS

J. Beckley, V. Kalinin, M. Lee, K. Voliansky, *Non-Contact Torque Sensors Based on SAW Resonators,* 2002 IEEE International Frequency Control Symposium and PDA Exhibition.

* cited by examiner

WIRELESS ACOUSTIC WAVE SENSOR SYSTEM FOR USE IN VEHICLE APPLICATIONS

TECHNICAL FIELD

Embodiments are generally related to acoustic wave sensing devices, such as Surface Acoustic Wave (SAW), Bulk Acoustic Wave (BAW), acoustic plate mode (APM) and other similar acoustic wave components. Embodiments are also related to wireless sensors and applications thereof. Embodiments are additionally related to pressure, friction, torque, acceleration, rotation rate and engine oil quality sensors utilized in automotive and aerospace applications.

BACKGROUND OF THE INVENTION

Surface acoustic wave (SAW) devices are utilized in a number of industrial, commercial, consumer and military applications. SAW technology Is generally characterized by its reliance on acoustic energy and electrical/acoustic transducers. SAW components are based on devices in which radio frequency signals are converted to acoustic signals and confined within a small substrate made from, for example, Lithium Niobate or other piezoelectric crystalline materials. SAW waves propagate at relatively low speed with reference to radio waves and, as such, a small substrate may produce relatively long time delays. SAW devices are useful, however, for example, in devices such as filters utilized in wireless applications and sensors utilized in various environmental detection applications, such as pressure, torque and/or temperature sensors.

SAW devices are manufactured from a SAW wafer. Such components are typically manufactured with quartz, which is utilized because the quartz provides for minimal hysteresis, high temperature stability, low creep, low aging and improved long-term stability.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide for an improved sensor apparatus and system.

It is another aspect of the present invention to provide for an acoustic wave sensor system.

The aforementioned aspects of the invention and other objectives and advantages can now be achieved as described herein. An acoustic wave sensor system, comprising a plurality of acoustic wave sensing devices for detecting a multiplicity of varying conditions and a common interrogation component that communicates with each acoustic wave sensing device among the plurality of acoustic wave sensor devices for providing an interrogation signal to each acoustic wave sensing device thereof. A transmitter and receiver unit can also be provided that communicates with the common interrogation component and the plurality of acoustic wave sensing devices and which transmits an interrogation signal from the common interrogation component to the at least one acoustic wave sensing device among the plurality of acoustic wave sensing devices and which receives sensor data from at least one acoustic wave sensing device. The common interrogation component can be, for example, a Digital Signal Processor (DSP), a transceiver, a RF switch, a mixer component, an oscillator and/or a Phase Locked Loop (PLL) circuit. The acoustic wave sensing device can be, for example, a SAW, BAW, or APM sensor. The system disclosed herein can be utilized within, for example, automotive applications and for identifying and detecting tire-pressure, engine in-cylinder pressure, friction, engine torque, acceleration, rotation rate, in-cabinet air quality, gaseous composition of fuel cell applications, and engine oil quality (e.g., viscosity, particulate and/or corrosivity). Even when one or more of the acoustic wave sensing devices utilize different modes of waves (e.g., SAW, BAW, APM, etc.), such acoustic wave sensing devices can share a common interrogation component (DSP, mixer, oscillator, PLL, DFT, etc.).

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 3($a$) illustrates a block diagram of an acoustic wave torque sensor system that can be implemented in accordance with one embodiment;

FIG. 3($b$) illustrates a block diagram of an acoustic wave pressure sensor system that can be implemented in accordance with one embodiment;

DETAILED DESCRIPTION OF THE INVENTION

The particular values and configurations discussed in these non-limiting examples can be varied and are cited merely to illustrate at least one embodiment of the present invention and are not intended to limit the scope of the invention.

Figure 1:
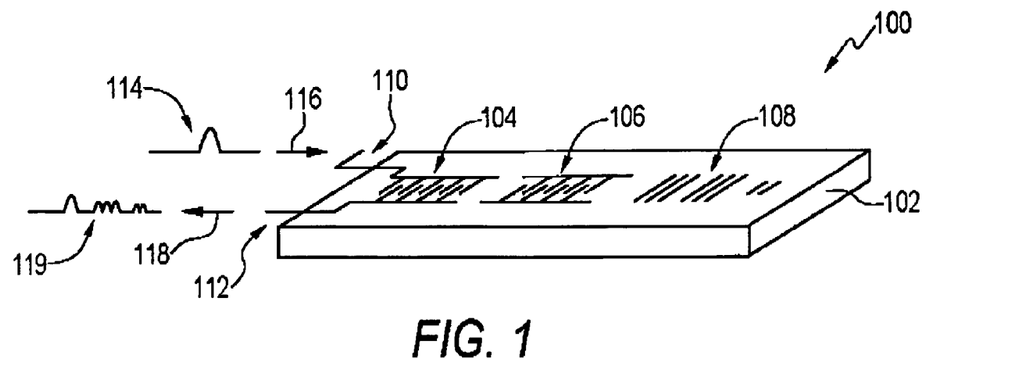
FIG. 1 illustrates a perspective view of an acoustic wave sensor apparatus that can be implemented in accordance with an embodiment.

FIG. 1 illustrates a perspective view of an acoustic wave sensor apparatus 100 that can be implemented in accordance with an embodiment. Apparatus 100 includes one or more acoustic wave resonators 104, 106, and 108 formed on a piezoelectric substrate 102. Each resonator 104, 106, and 108 can be configured on substrate 102 as an Interdigital Transducer (IDT) or an IDT electrode. Resonator or IDT 104 can be connected to antenna 110, 112. A Radio Frequency (RF) interrogation signal 114 can be provided to antenna 110 as indicated by arrow 116.

An RF response signal 119 can be transmitted from antenna 112 as indicated by arrow 115. Note that resonator 108 can be configured as a reflector rather than an IDT, depending upon design considerations. Apparatus 100 therefore constitutes a passive wireless acoustic wave sensor device. Apparatus 100 may be, for example, a SAW, BAW, APM or other similar acoustic wave sensor devices, depending upon design considerations. If apparatus 100 is implemented as an Acoustic Plate Mode (APM) device rather than a SAW or BAW device, substrate 102 can be provided as a quartz plate.

Piezoelectric substrate 102 can be formed from a variety of substrate materials, such as, for example, quartz, lithium niobate ($LiNbO_3$), lithium tantalite ($LiTaO_3$), $Li_2B_4O_7$, $GaPO_4$, langasite ($La_3Ga_5SiO_{14}$), ZnO, and/or epitaxially grown nitrides such as Al, Ga or Ln, to name a few. Interdigital transducers 104, 106 and/or 108 can be formed from materials, which are generally divided into three groups. First, IDT 104, 106 and/or 108 can be formed from a metal group material (e.g., Al, Pt, Au, Rh, Ir Cu, Ti, W, Cr, or Ni). Second, IDT 104, 106 and/or 108 can be formed from alloys such as NiCr or CuAl. Third, IDT 104, 106 and/or 108 can be formed from metal-nonmetal compounds (e.g., ceramic electrodes based on TiN, $CoSi_2$, or WC).

Figure 2:
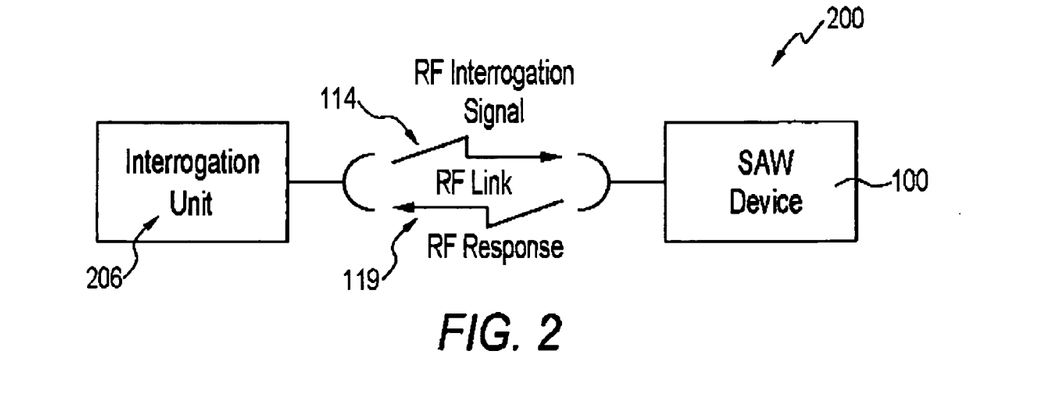
FIG. 2 illustrates a block diagram of an acoustic wave sensor system that can be implemented in accordance with a preferred embodiment.

FIG. 2 illustrates a block diagram of an acoustic wave sensor system 200 that can be implemented in accordance with a preferred embodiment. Note that in FIGS. 1-2, identical or similar parts or components are generally indicated by identical reference numerals. As indicated above, component 108 may or may not be provided as an IDT. This depends on the choice of the designer wishing to Implement varying embodiments. If component 108 is provided in the context of a reflector configuration upon substrate 102 rather than as an IDT or resonator, then a high frequency electromagnetic wave (e.g., interrogation signal 114) can be emitted by the interrogation unit 205 depicted in FIG. 2, and is received by the antenna 110 of the acoustic wave transponder or IDT 104.

The IDT 104 that is connected to the antenna 110 transforms, with the assistance of an inverse piezoelectric effect, the received signal into an acoustic wave, such as, for example, a SAW. The signal (SAW, BAW, etc.) propagates on the crystal substrate 102 towards the reflector or reflector components 108. The reflector(s) 108 can be placed in a particular pattern that reflects part of the incoming wave. What returns to the IDT 104 and/or 106 is a high-frequency series of echoes, which are transduced back into an electromagnetic signal. This is the response signal 119 that is sent through the antenna and back to the interrogation unit 206 depicted in FIG. 2. The RF response signal 119 carries information about the location and quantity of the reflections together with the information of the propagation and reflection properties of the acoustic wave signal. The interrogation unit 206 evaluates the amplitude, frequency and time of the signal and determines the identification number or calculates the sensor value. Note that interrogation unit 206 can be utilized in the context of system 200 whether or not component 108 is implemented as a reflector or an IDT.

The acoustic wave sensor or sensing device 100 can be implemented in the context of a variety of different types of sensing applications. For example, the acoustic wave sensing device 100 can be implemented as a gaseous composition sensor, such as, for example, a hydrogen sensor, a carbon monoxide sensor, an oxygen sensor, an exhaust NOx sensor, or an exhaust $SO_2$ sensor. The acoustic save sensing device 100 can also be implemented as a shaft torque sensor such as that depicted in FIG. 3(a) or an acceleration sensor. The acoustic wave sensing device 100 can also be configured to function as a tire pressure sensor, an engine cylinder pressure sensor or a tire friction sensor.

The acoustic wave sensing device 100 can also be implemented as an engine oil quality sensor, such as, for example, an oil viscosity sensor, a total acid number (TAN) sensor, a total base number (TBN) sensor, or an oil particulate sensor. The acoustic wave sensing device 100 can also be implemented as a SAW sensor, a BAW sensor, an APM sensor or an SH-SAW sensor, depending upon design considerations. The acoustic wave sensing device 100 can also be, for example, a cantilever sensor, a cantilever sensor array, or a tuning fork sensor, again depending upon design considerations.

Figure 3A:
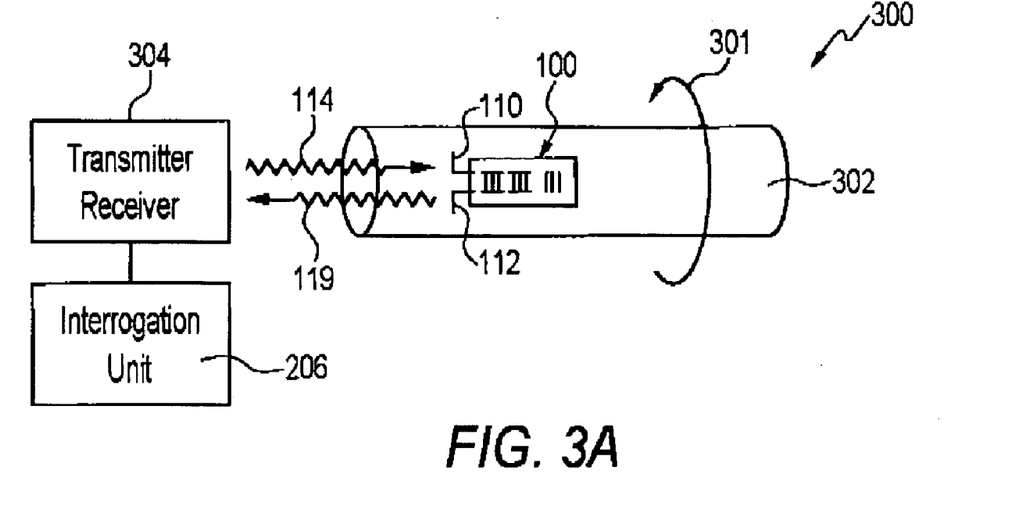

FIG. 3(a) illustrates a block diagram of an acoustic wave torque sensor system 300 that can be implemented in accordance with one embodiment. Note that in FIGS. 1-3(b), identical or similar parts or elements are generally indicated by identical reference numerals. System 300 generally includes a component 302 that is subject to torque as indicated by arrow 301. Component 302 can be, for example, a shaft utilized in automotive engine or aerospace application. The acoustic wave sensor device 100, which may be, for example, a SAW, BAW, APM and/or other acoustic wave sensor apparatus can be located on the component 302 in order to obtain torque data. The ability to detect torque plays an important role in automatic controllers for a great variety of complex mechanical systems. In the configuration depicted in FIG. 3(a), the interrogation unit 206 is shown in communication with a transmitter/receiver unit 304 which transmits and receives respective signals 114, 119 from antennas 110, 112 associated with acoustic wave sensor apparatus 100.

Figure 3B:
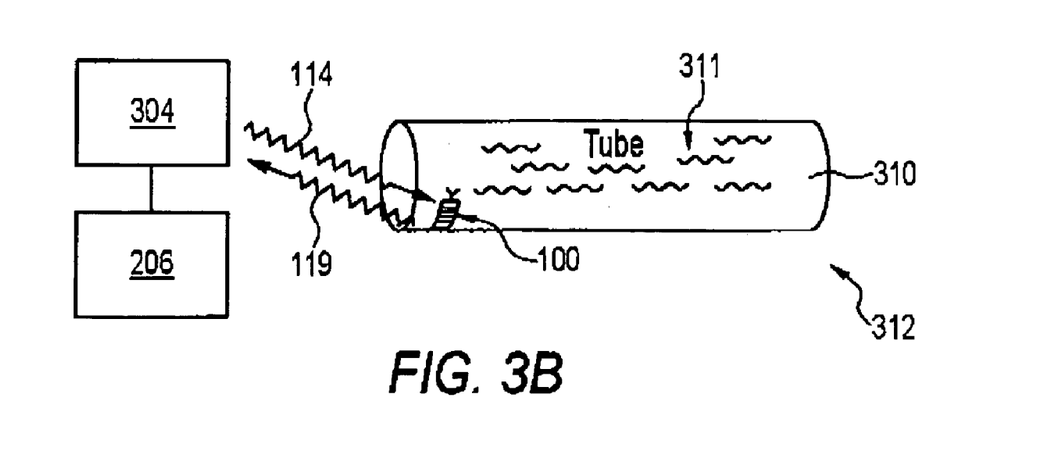

FIG. 3(b) illustrates a block diagram of an acoustic wave pressure sensor system 312 that can be implemented in accordance with another embodiment. The components depicted in FIG. 3(b) are similar to those depicted in FIG. 3(a), the difference being that the acoustic wave sensor apparatus 100 is located within a tube 310 through which a fluid 311 flows. The acoustic wave sensor apparatus 100 depicted in FIG. 3(b) is thus utilized for detecting pressure within tube 310.

Figure 4:
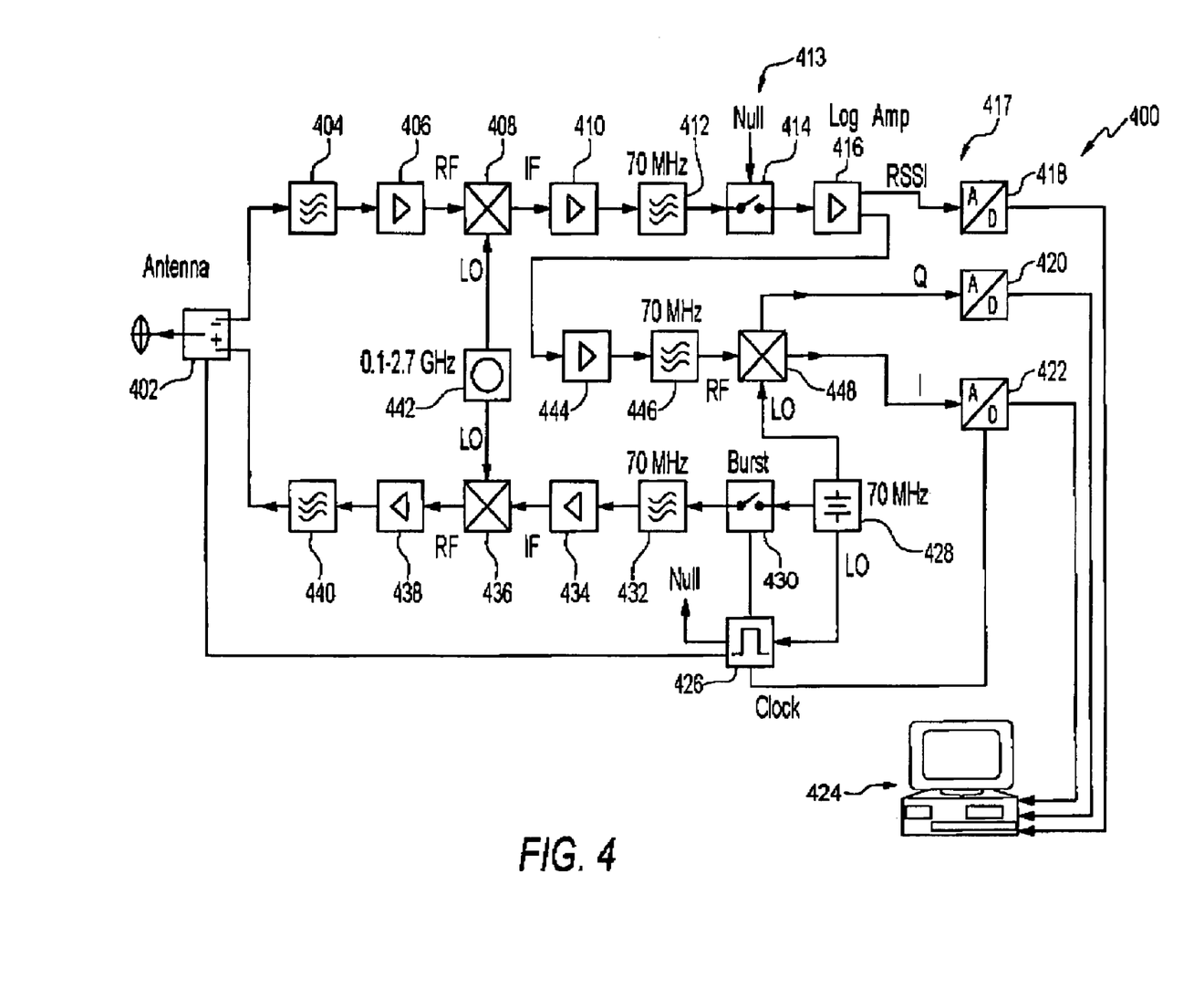
FIG. 4 illustrates a block diagram of an acoustic wave pressure sensor system that can be implemented in accordance with the embodiment depicted in FIG. 3($a$)

FIG. 4 illustrates a block diagram of an acoustic wave pressure sensor system 400 that can be implemented in accordance with the embodiment depicted in FIG. 3(a). System 400 generally includes an antenna 402 that provides a signal 404 that is provided as RF data through an RF stage 406 and then an IF stage 408 followed by another RF stage 410 and a stage 412 at a frequency of approximately 70Mhz. A null signal 412 can be provided to a component or stage 414 and then to a logarithmic amplifier 416 and finally to an Analog-to-Digital (ND) converter 418. Note that several other A/D converters 420, 422 are also provided in the context of system 400. A 100 Mhz-2.7Ghz frequency synthesizer 442 can also be provided which provides a signal to stage 408 (which may be a mixer). Components 444, 446 and 448 are also provided along with components 426 to 440. Note that component 426 can generate a clock signal, while component 430 may function as a switch that provides a burst signal. Data output from A/D converters 418, 420, 422 can be provided to a computer 424 for processing.

Note that the interrogation unit utilized in the context of system 400 can be implemented as, for example, an interrogation unit similar to those utilized in radar applications.

Interrogation units can be constructed, which are based on pulse radars, pulse compression radar and FMCW radar architectures if desired, although non-radar interrogation units can also be utilized, depending upon the desired embodiments. System 400 can be utilized to achieve optimal values over a broad frequency range. In the example depicted in FIG. 4, system 400 is provided in the context of a heterodyne receiver architecture with a 70 MHz IF stage and a limiter amplifier with radio signal strength indicator output (RSSI) 417.

With an exchangeable IF SAW filter, a system bandwidth of 36 MHz can be achieved. To compensate coherent crosstalk in the IF-stage as well as the DC-offset of the mixer 408 following the use of logarithmic amplifier 416 and a DC-offset of the A/D converters 418, 420, and/or 422, a GaAS FET switch 430 can be inserted between an IF filter and the logarithmic amplifier 416. It can be appreciated that the configuration depicted in FIG. 4 represents only one example and is not considered a limiting feature of the embodiments disclosed herein.

Figure 5:
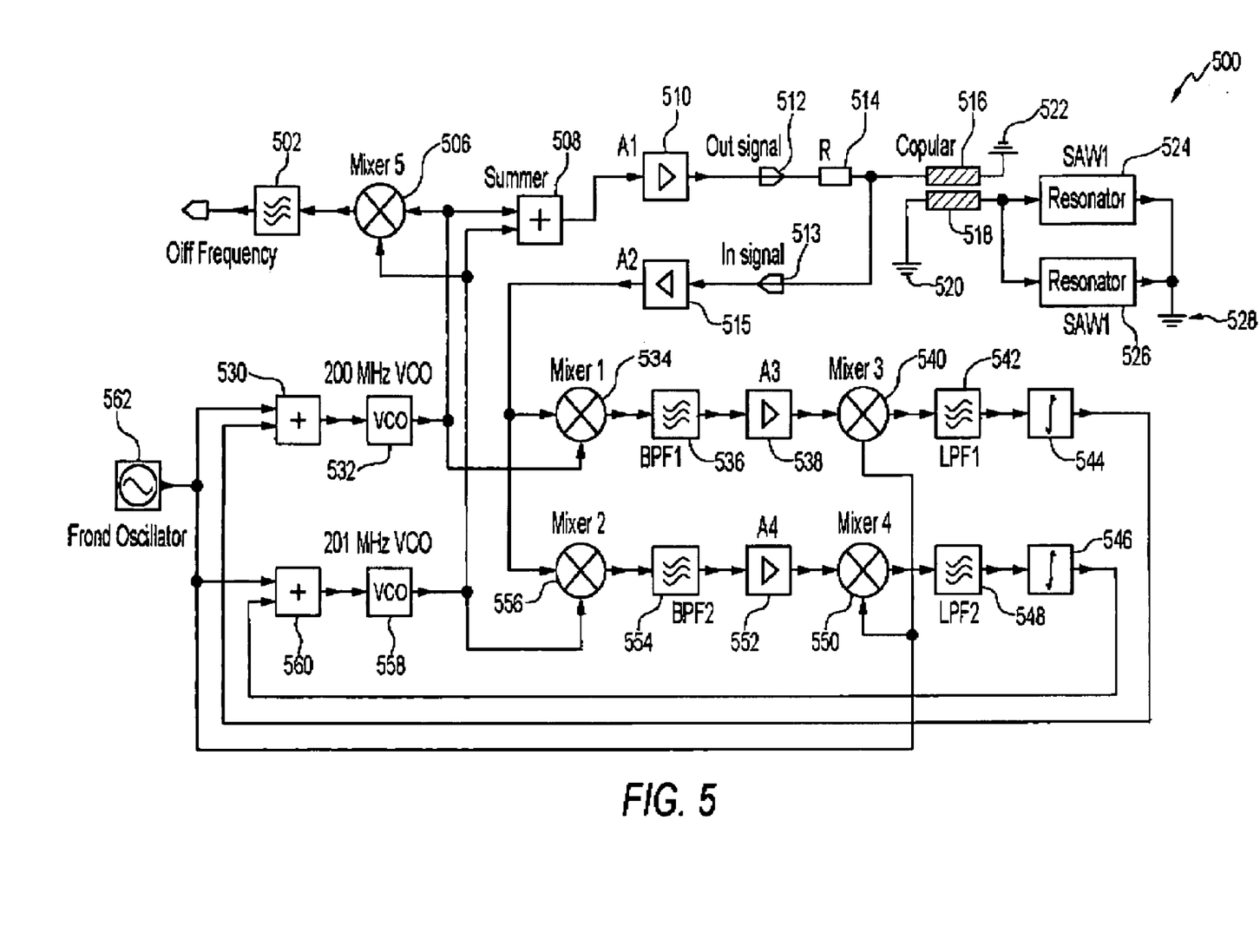
FIG. 5 illustrates a block diagram of an acoustic wave torque sensor system that can be implemented in accordance with the embodiment depicted in FIG. 3($b$)

FIG. 5 illustrates a block diagram of an acoustic wave torque sensor system 500 that can be implemented in accordance with the embodiment depicted in FIG. 3(b). In the configuration depicted in FIG. 5, one or more SAW resonators 524 and 526 are provided. Note that such resonators are analogous to resonators 104, 106 depicted in FIG. 1. Resonators 524 and 526 are connected to a ground 528. Coupler components 516 and 518 can also be provided in the context of system 500. Coupler 516, for example, is connected to a ground 522 and coupler 518 is connected to a ground 520.

An output signal 512 can be generated by an amplifier 510 and sent through a resistor component 514 to coupler 516, and an input signal 513 can be generated from coupler 516 and input to an amplifier 515. Note that a mixer 534 can mix signals generated from amplifier 515 and also from a VCO 532 that receives summation data from a summation unit 530. Similarly, a mixer 506 generates data that is transmitted to a summation unit 508 that provides output data to amplifier 510 that in turn forms a part of the output signal 512 described above.

Data from mixer 506 is also output as a differential frequency 502. An oscillator 562 is also provided, which provides a signal to the summation unit 530 and to another summation unit 560. Output from the summation unit 560 is provided to a VCO 558 which in turn provides data to a mixer 556 and to the summation unit 508. Data generated from mixer 556 is provided as a differential frequency 554 and then to an amplifier 552 and thereafter to a mixer 550 whose output generates a differential frequency 548, followed by input to an integrator 546 whose output is provided to the summation unit 560.

Output from the mixer 534 is provided as a differential frequency 536 and then to an amplifier 538. The output from amplifier 538 is provided as input to a mixer 540 whose output produces a differential frequency 542 that is fed to an integrator 544. Output from the integrator 544 is then fed to the summation unit 530 along with output from the oscillator 562.

Figure 6:
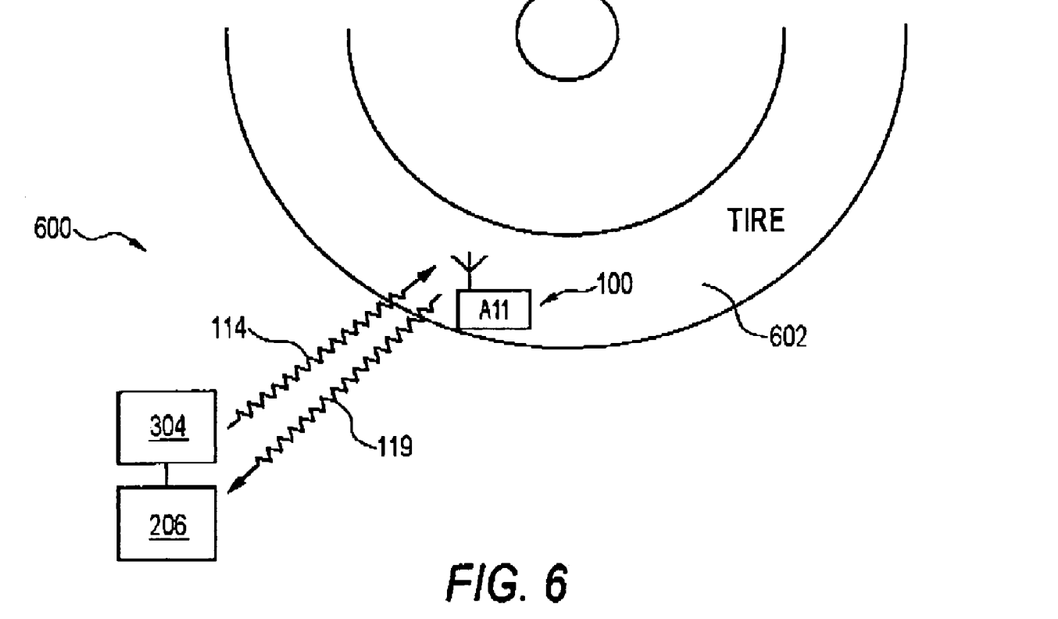
FIG. 6 illustrates a block diagram of a tire condition sensor system that can be implemented in accordance with another embodiment.

FIG. 6 illustrates a block diagram of a tire condition sensor system 600 that can be implemented in accordance with another embodiment. Note that in FIGS. 1-6, identical or similar parts or elements are generally indicated by identical reference numerals. System 600 generally incorporates the use of the acoustic wave sensor apparatus 100, which is located within a tire 602 and for detecting environmental conditions such as pressure and/or temperature within tire 602.

The system disclosed herein can be utilized within, for example, automotive applications and for identifying and detecting pressure, friction, engine torque, acceleration, rotation rate and engine oil quality (e.g., viscosity and/or corrosivity). Even when one or more of the acoustic wave sensing devices utilize different modes of waves (e.g., SAW, BAW, APM, etc.), such acoustic wave sensing devices can share a common interrogation component (DSP, mixer, oscillator, PLL, DFT, etc.).

The systems disclosed herein can be designed to lower the cost of component implementation by designing the entire system together. For example, if an oil quality sensor is added to a vehicle system, the interrogation component or interrogation unit 206 can be shared by the existing torque sensor. Thus, the cost of the wireless oil quality sensor can be close to or even lower than a wired oil quality sensor system. In another embodiment, the system can be modified to incorporate a wireless and passive tire pressure sensor such as that depicted in FIG. 6. In still a further alternative embodiment, the system can be modified to include gas sensors, such as hydrogen and CO sensors inside a vehicle cabinet (e.g., in the case of fuel cell applications), along with emission gas sensors for emission control. Further, one or more such interrogation units 206 can be connected with a system bus (e.g., CAN bus) such as a CAN-SAW wireless bush/antenna throughout an automotive vehicle or aerospace body frame.

Figure 7:
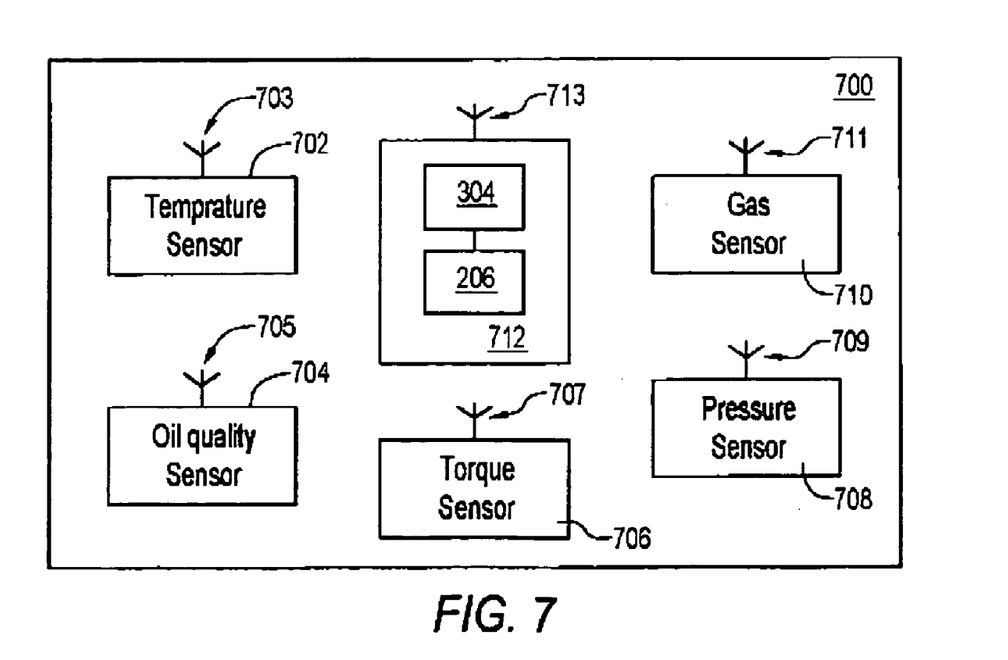
FIG. 7 illustrates a system composed of a unit comprising an interrogation unit 206 and a transmitter/receiver unit in accordance with another embodiment.

FIG. 7, for example, illustrates a system 700 composed of a unit 712 composed of the interrogation unit 206 and the transmitter/receiver unit 304. An antenna 713 is associated with unit 712 and transmits data to and from a plurality of acoustic wave sensing devices, such as an acoustic wave temperature sensor 702, an acoustic wave oil quality sensor 704, and an acoustic wave torque sensor 706, an acoustic wave pressure sensor 708 and/or an acoustic wave gas sensor 710. Note that the acoustic wave temperature sensor 702, the acoustic wave oil quality sensor 704, the acoustic wave torque sensor 706, the acoustic wave pressure sensor 708 and the acoustic wave gas sensor 710 are respectively associated with antennas, 703, 705, 707, 709, and 711. Each of the sensors 702-710 depicted in FIG. 7 can function structurally and similarly to the acoustic wave sensor 100 described earlier.

It will be appreciated that variations of the above-disclosed and other features and functions, or alternatives thereof, may be desirably combined into many otherdifferent systems or application. Also that various presently unforseen or unanticipated alternatives, modifications, variations or improvements therein may be subsequently made by those skilled in the art which are also intended to be encompassed by the following claims.

What is claimed is:

1. An acoustic wave sensor system, comprising:
a plurality of acoustic wave sensing devices for detecting a multiplicity of varying conditions, wherein each acoustic wave sensing device among said plurality of acoustic wave sensing devices comprises an independent component for detecting at least one condition among said multiplicity of varying conditions;
a common interrogation component that communicates with said each acoustic wave sensing device among said plurality of acoustic wave sensor devices for providing an interrogation signal to said each acoustic wave sensing device thereof wherein said each acoustic wave sensing device utilizes at least one of a plurality of wave modes; and a transmitter and receiver unit that communicates with said common interrogation component and said plurality of acoustic wave sensing devices and which transmits an interrogation signal from said common interrogation component to at least one acoustic wave sensing device among said plurality of acoustic wave sensing devices and which receives sensor data from said at least one acoustic wave sensing device.

2. The system of claim 1 wherein said common interrogation component comprises a Digital Signal Processor (DSP).

3. The system of claim 1 wherein said common interrogation component comprises at least one mixer component.

4. The system of claim 1 wherein said common interrogation component comprises an oscillator.

5. The system of claim 1 wherein said common interrogation component comprises at least one of the following: a Phase Locked Loop (PLL) circuit, a transceiver, or an RF switch.

6. The system of claim 1 wherein said at least one acoustic wave sensing device comprises a SAW sensor.

7. The system of claim 1 wherein said at least one acoustic wave sensing device comprises a BAW sensor.

8. The system of claim 1 wherein said at least one acoustic wave sensing device comprises an APM sensor.

9. The system of claim 1 wherein said at least one acoustic wave sensing device comprises an SH-SAW sensor.

10. The system of claim 1 wherein said at least one acoustic wave sensing device comprises a cantilever sensor.

11. The system of claim 10 wherein said cantilever sensor comprises a cantilever sensor array.

12. The system of claim 1 wherein said at least one acoustic wave sensing device comprises a tuning fork sensor.

13. An acoustic wave sensor system, comprising:
a plurality of acoustic wave sensing devices for detecting a multiplicity of varying conditions, wherein at least one acoustic wave sensing device among said plurality of acoustic wave sensing devices comprises a Surface Acoustic Wave (SAW) sensor;

an antenna configured upon each acoustic wave sensing device among said plurality of acoustic wave sensing devices wherein said each acoustic wave sensing device of said plurality of acoustic wave sensing devices comprises an independent component for detecting at least one condition among said multiplicity of varying conditions;

a common interrogation component that communicates with said each acoustic wave sensing device among said plurality of acoustic wave sensor devices for providing an interrogation signal to said each acoustic wave sensing device thereof, wherein said common interrogation component comprises at least one of the following: a Digital Signal Processor (DSP), at least one mixer component, an oscillator, or a Phase Locked Loop (PLL) circuit; and a transmitter and receiver unit that communicates with said common interrogation component and said plurality of acoustic wave sensing devices and which transmits an interrogation signal from said common interrogation component to said at least one acoustic wave sensing device among said plurality of acoustic wave sensing devices and which receives sensor data from said at least one acoustic wave sensing device.

14. The system of claim 13 wherein said at least one acoustic wave sensing device comprises at least one of the following: a tire pressure sensor, a tire friction sensor, an engine cylinder pressure sensor, an engine oil quality sensor, a shaft torque sensor, an acceleration sensor, or a gaseous composition sensor.

15. An acoustic wave sensing method, comprising:
configuring on a piezoelectric substrate a plurality of acoustic wave sensing devices for detecting a multiplicity of varying conditions wherein each acoustic wave sensing device among said plurality of acoustic wave sensing devices comprises utilizes at least one of a plurality of wave modes and wherein said each acoustic wave sensing device among said plurality of acoustic wave sensing devices comprises an independent component for detecting at least one condition among said multiplicity of varying conditions;

communicating with said each acoustic wave sensing device among said plurality of acoustic wave sensor devices utilizing a common interrogation component for providing an interrogation signal to said each acoustic wave sensing device thereof; and providing a transmitter and receiver unit that communicates with said common interrogation component and said plurality of acoustic wave sensing devices and which transmits an interrogation signal from said common interrogation component to at least one acoustic wave sensing device among said plurality of acoustic wave sensing devices and which receives sensor data from said at least one acoustic wave sensing device.

16. The method of claim 15 wherein said common interrogation component comprises a Digital Signal Processor (DSP).

17. The method of claim 15 wherein said common interrogation component comprises at least one mixer component.

18. The method of claim 15 wherein said common interrogation component comprises an oscillator.

19. The method of claim 15 wherein said common interrogation component comprises at least one of the following: a Phase Locked Loop (PLL) circuit, a transceiver, or an RF switch.

20. The method of claim 15 wherein said at least one acoustic wave sensing device comprises at least one of the following: a SAW sensor, a BAW sensor, an APM sensor, or an SH-SAW sensor; and an antenna respectively configured upon said each acoustic wave sensing device among said plurality of acoustic wave sensing devices.

* * * * *

UNITED STATES PATENT AND TRADEMARK OFFICE
CERTIFICATE OF CORRECTION

PATENT NO. : 7,343,804 B2  Page 1 of 1
APPLICATION NO. : 11/274786
DATED : March 18, 2008
INVENTOR(S) : James Z T Liu et al.

It is certified that error appears in the above-identified patent and that said Letters Patent is hereby corrected as shown below:

In Column 7, line 12, delete "device." and add "device and wherein said transmitter and receiver unit is capable of transmitting said interrogation signal and receiving said sensor data from said each acoustic wave sensing device wherein different wave modes are by utilized by more than one acoustic wave sensing device of said each acoustic wave sensing device."

In Column 8, line 8, delete. "device." and add "device and wherein said transmitter and receiver unit is capable of transmitting said interrogation signal and receiving said sensor data from said each acoustic wave sensing device wherein different wave modes are by utilized by more than one acoustic wave sensing device of said each acoustic wave sensing device."

In Column 8, line 38, delete "device." and add "device and wherein said transmitter and receiver unit is capable of transmitting said interrogation signal and receiving said sensor data from said each acoustic wave sensing device wherein different wave modes are by utilized by more than one acoustic wave sensing device of said each acoustic wave sensing device."

Signed and Sealed this

Twenty-fifth Day of November, 2008

JON W. DUDAS
*Director of the United States Patent and Trademark Office*